United States Patent [19]

Caldirola et al.

[11] Patent Number: 5,171,752
[45] Date of Patent: Dec. 15, 1992

[54] BENZHYDRYL DERIVATIVES HAVING CALMODULIN INHIBITOR PROPERTIES

[75] Inventors: Patricia Caldirola, Köln; Raimund Mannhold, Düsseldorf, both of Fed. Rep. of Germany; Hendrik Timmerman, Voorschoten, Netherlands

[73] Assignee: AKZO N.V., Arnhem, Netherlands

[21] Appl. No.: 732,856

[22] Filed: Jul. 19, 1991

[30] Foreign Application Priority Data

Jul. 19, 1990 [EP] European Pat. Off. ........... 90201954

[51] Int. Cl.$^5$ .................. A61K 31/135; C07C 323/26
[52] U.S. Cl. ..................................... 514/648; 564/317
[58] Field of Search ......................... 564/317; 514/648

[56] References Cited

U.S. PATENT DOCUMENTS

3,666,811  5/1972  van der Stelt ....................... 564/317

FOREIGN PATENT DOCUMENTS

1028913  5/1966  United Kingdom .

OTHER PUBLICATIONS

N. V. Koninklyke, Chemical Abstracts, vol. 72 (1970) 1002684.
Corsano et al., Chemical Abstracts, vol. 112 (1989) 118353b.
Kansal et al., "Possible antihypertensive agents: Synthesis of N-aralkyl-beta Substituted Phenylethylamines and N-alkyl/acyl-6,7-dimethoxy-1-[alpha--phenyl-beta-substituted phenyl)ethyl]-1,2,3,4-tetrahydroisoquinolines", Chemical Abstracts, vol. 96, No. 9, Mar. 1, 1982, p. 592, Abstract No. 68781t, U.S.A.
Barron et al., D. I., "Compounds Affecting the Central Nervous System. III. Substituted 1,1-Diaryl-t-aminopropanols and Related Compounds", Journal of Med. Chemistry, vol. 8, Nov. 1985, pp. 836-841, U.S.A.
Gualtieri, F. et al., "SAR Studies in the Field of Calcium(II) Antagonists. Effect of Modifications at the Tetrasubstituted Carbon of Verapamil-like Compounds", Journal of Medicinal Chemistry, vol. 28, No. 11, pp. 1621-1628, U.S.A., 1985.
Zenno et al., "Tertiary bis(phenylalkyl)amines", Chemical Abstracts, vol. 82, No. 7, Feb. 17, 1975, p. 406, No. 430412, U.S.A.

Primary Examiner—Richard L. Raymond
Attorney, Agent, or Firm—Donna Bobrowicz

[57] ABSTRACT

The invention relates to a benzhydryl derivative having the formula

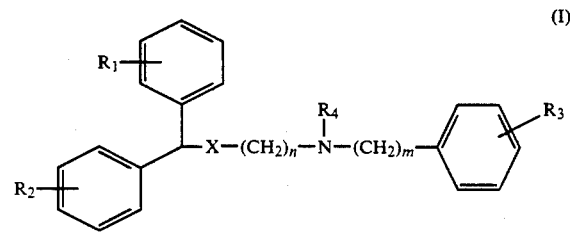

wherein
each of the groups $R_1$, $R_2$, and $R_3$ represents one to four substituents independently selected from the group consisting of hydrogen, lower alkyl, halogen, and $CF_3$, and at least one of the groups $R_1$, $R_2$, and $R_3$ is halogen or $CF_3$;
$R_4$ represents hydrogen or methyl;
n is 2, 3, or 4;
m is 1, 2, or 3; and
X represents O or S;
or its pharmaceutically acceptable salts.

The benzhydryl derivative of the invention can be used to treat patients who are suffering from diseases which are influenced by calmodulin.

6 Claims, No Drawings

BENZHYDRYL DERIVATIVES HAVING CALMODULIN INHIBITOR PROPERTIES

The invention relates to benzhydryl derivatives having the formula

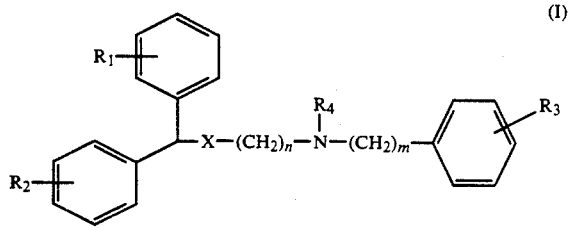

wherein
each of the groups $R_1$, $R_2$, and $R_3$ represents one to four substituents independently selected from the group consisting of hydrogen, lower alkyl, halogen, and $CF_3$, and at least one of the groups $R_1$, $R_2$, and $R_3$ is halogen or $CF_3$;
$R_4$ represents hydrogen or methyl;
n is 2, 3, or 4;
m is 1, 2, or 3; and
X represents O or S;
or its pharmaceutically acceptable salts.

The invention further concerns a process for the preparation of said benzhydryl derivatives, pharmaceutical preparations containing the same, and the use thereof, as well as a method of treating patients with such benzhydryl derivatives.

For the treatment of angina and ischaemia the use of calcium antagonists is a therapy of choice. Recently it became known, however, that the efficacy of the most effective drugs may be dependent upon the reduction of the effect of calcium ions through inhibition of calmodulin, rather than from the reduction of the availability of calcium ions through $Ca^{2+}$ channel inhibition. Thus the more potent blockers of the enzyme calmodulin have advantages over the existing therapy in terms of efficacy, and given that calmodulin is a calcium acceptor protein in platelets but not in cardiac muscle, calmodulin antagonists possess anti-aggregation activity whilst being devoid of marked negative inotropic activity. This larger profile of activity over the existing calcium entry blockers currently used in angina pectoris therapy provides not only symptomatic relief, but also interferes with the primary causes responsible for ischaemic heart disease.

Related benzhydryl derivatives with calmodulin inhibitor activity are known. The most conspicuous examples are fendiline (U.S. Pat. No. 3,262,977) and prenylamine (German patent No. 1,100,031), both of which are marketed products with vasodilatory activity. Fendiline and prenylamine bind to L-type calcium channels in the sarcolemma of excitable cells and proved also to possess calmodulin inhibitor activity.

Even more related benzhydryl derivatives were recently disclosed by S. Corsano et al., Arch. Pharm., 322, 873-878 (1989). These compounds, which are reported to have Ca-antagonist activity, have unsubstituted benzhydryl and phenyl rings.

The benzhydryl derivatives of this invention, however, are in general about 3-50 times more potent with respect to their calmodulin inhibitor activity than the known compounds fendiline and prenylamine, and approx. 2-5 times more potent than the compounds disclosed by Corsano et al. The compounds of this invention, therefore, are better candidates for the treatment of diseases which are influenced by calmodulin, such as angina, ischaemia, asthma, gastrointestinal disorders, and for the recovery of the sensitivity of tumors for cytostatics.

The term halogen used in the definition of formula I means fluorine, chlorine, bromine or iodine. Chlorine and in particular fluorine are the preferred halogens.

The term lower alkyl means an alkyl group selected from methyl, ethyl, propyl, isopropyl, butyl, sec-butyl, and tert-butyl. Methyl is the preferred alkyl group.

Each of the aromatic rings may independently be substituted with one to four substituents, that is to say that each of the groups $R_1$, $R_2$, and $R_3$ may represent more than one substituent. Preferred compounds have aromatic rings with none or one substituent, provided that at least one of the aromatic rings is substituted with halogen or $CF_3$. Preferably, $R_3$ is halogen or $CF_3$. Most preferred are benzhydryl derivatives having $R_3$ is $CF_3$.

Preferred compounds further have X is S, and n and m are 2 or 3.

Of the preferred compounds are specifically mentioned: N-[2-(diphenylmethylthio)ethyl]-2-(trifluoromethyl)-benzeneethanamine;

N-[2-(bis(4-fluorophenyl)methylthio)ethyl]-2-(trifluoromethyl)benzeneethanamine; and N-[2-(bis(4-fluorophenyl)methylthio)ethyl]-3-(trifluoromethyl)benzeneethanamine.

The novel compounds of formula I may be isolated from a reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, and ascorbic acid.

The compounds of this invention may possess a chiral carbon atom when $R_1$ and $R_2$ are different, and may therefore be obtained as a pure enantiomer, or as a mixture of enantiomers, among which the racemic mixture. Methods for obtaining the pure enantiomers are well known in the art, e.g. synthesis with chiral induction, crystallization of salts which are obtained from optically active acids and the racemic mixture, or by chromatography using chiral columns. Compounds having the same groups $R_1$ and $R_2$ are preferred, because they lack such chiral carbon atom.

The benzhydryl derivatives of the invention may be prepared by methods commonly known for the preparation of analogous compounds.

A suitable process for the preparation of these benzhydryl derivatives is the condensation of an amine having formula II

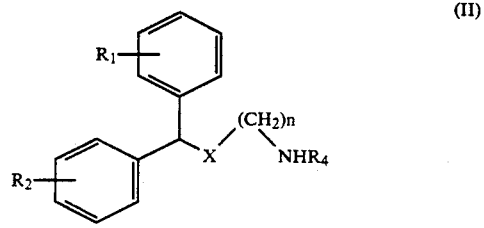

or an addition salt thereof, in which $R_1$, $R_2$, $R_4$, n, and X have the previously given meanings, with an aldehyde (when $R_4$ is hydrogen) or halide having formula III

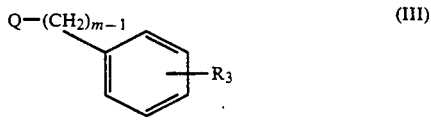

in which m and $R_3$ have the previously given meanings and Q represents the aldehyde group CHO or the halide group $CH_2Hal$, in which Hal denotes chlorine, bromine or iodine. When Q is an aldehyde group the condensation is performed under reductive conditions by applying any suitable reduction means, such as sodium borohydride or sodium cyanoborohydride in a suitable solvent like tetrahydrofuran or methanol. When Q is a halide group, the condensation is performed under slightly alkaline conditions, for example with potassium carbonate in methyl isobutyl ketone.

The compounds of the invention may also be prepared by the condensation of an amine having formula IV

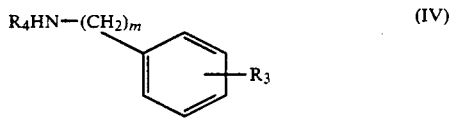

or a addition salt thereof, in which m, $R_3$, and $R_4$ have the previously given meanings, with an aldehyde (when $R_4$ is hydrogen) or halide having formula V

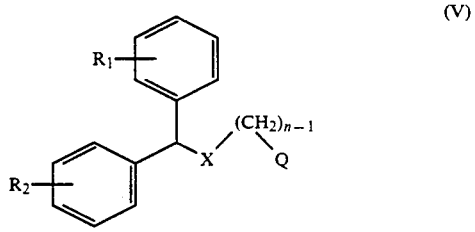

in which $R_1$, $R_2$, n, Q, and X have the previously given meanings, under conditions which are similar to those described previously for the condensation of compounds II and III.

Compounds having formula I in which $R_4$ is hydrogen can be converted into compounds having formula I in which $R_4$ is methyl, by methylation in a manner known per se, for instance by reaction with methyl iodide in a suitable solvent, or by reaction with a mixture of formaldehyde and formic acid.

The preparation of compounds II-V is performed according to known procedures, such as described in Tetrahedron, 23, 3923-29 (1967) and J. Am. Chem Soc., 72, 2786-88 (1950), and as embodied in the examples.

The compounds of the invention may be administered enterally or parenterally, and for humans preferably in a daily dosage of 0.001-10 mg per kg body weight. Mixed with pharmaceutically suitable auxiliaries, e.g. as described in the standard reference, Chase et al., Remington's Pharmaceutical Sciences, the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

The invention is further illustrated by the following examples.

EXAMPLE 1

N-2-(diphenylmethylthio)ethyl]-2-(trifluoromethyl)-benzeneethanamine (Z)-2-butenedioate (1:1) salt.

a) 2-Mercaptoethanamine hydrochloride (0.10 mol) and diphenylmethanol (0.105 mol) were dissolved in glacial acetic acid (100 ml) followed by the addition of $BF_3$ in diethyl ether (0.11 mol of $BF_3$). The stirred solution was heated at 80-90° C. for 15 min. The crude product was precipitated by the addition of ether (1.2 l). The white salt was filtered off and dried in vacuo over sodium hydroxide pellets. This dried salt was dissolved in hot ethanol, and the solution was then filtered and concentrated yielding 80% of the hydrochloride salt. The compound was recrystallized from ethyl acetate to give 2-(diphenylmethylthio)ethanamine hydrochloride, m.p. 167°-168° C. The free base was obtained by dissolving the hydrochloride salt in hot water, addition of sodium carbonate to pH 10, followed by extraction with diethyl ether.

b) 2-(trifluoromethyl)ethanol was stirred overnight at room temperature in diethyl ether in the presence of phosphorous tribromide. The ether phase was washed twice with 5% aq. sodium hydroxide and water, dried over sodium sulfate and concentrated. The bromide was purified by distillation to obtain 1-(2-bromoethyl)-2-(trifluoromethyl)benzene, b.p. 80° C. at 0.4 mm Hg.

c) A mixture of 2-(diphenylmethylthio)ethanamine (0.1 mol), 1-(2-bromoethyl)-2-(trifluoromethyl)benzene (0.1 mol) and anhydrous potassium carbonate (10 g) in methyl isobutyl ketone (50 ml) was refluxed under nitrogen for 40 hours. The reaction mixture was cooled, poured into a beaker containing ice, followed by the addition of ethyl acetate. The layers were separated, the organic phase was washed with water and brine, dried over potassium carbonate, and concentrated to an oil. The compound was purified by flash column chromatography and converted into the N-[2-(diphenylmethylthio)ethyl]-2-(trifluoromethyl)-benzeneethanamine (Z)-2-butenedioate (1:1) salt, m.p. 145°-146° C., in 50% yield.

EXAMPLE 2

In an analogous manner as described in Example 1 were prepared:

N-[2-(bis(4-fluorophenyl)methylthio)ethyl]benzenepropanamine (Z)-2-butenedioate (1:1) salt. m.p. 155°-157° C.

N-[2-(bis(4-fluorophenyl)methylthio)ethyl]-2-(trifluoromethyl)benzeneethanamine (Z)-2-butenedioate (1:1) salt. m.p. 151°-152° C.

N-[2-(bis(4-fluorophenyl)methylthio)ethyl]-3-(trifluoromethyl)benzeneethanamine (Z)-2-butenedioate (1:1) salt. m.p. 129°-131° C.

N-[2-(diphenylmethylthio)ethyl]-2-fluorobenzeneethanamine (Z)-2-butenedioate (1:1) salt.

N-[2-(bis(4-fluorophenyl)methylthio)ethyl]-N-methyl-3-(trifluoromethyl)benzeneethanamine (Z)-2-butenedioate (1:1) salt.

N-[2-(bis(4-fluorophenyl)methylthio)ethyl]-N-methyl-2-(trifluoromethyl)benzeneethanamine (Z)-2-butenedioate (1:1) salt.

EXAMPLE 3

N-[2-(bis(4-fluoroohenyl)methoxy)ethyl]benzeneethanamine (Z)-2-butenedioate

Bis(4-fluorophenyl)methanol was refluxed in toluene with an equimolar amount of bromoethanol in presence of a catalytic amount of p-toluenesulphonic acid. The mixture was refluxed for 12 hrs. in a Dean-Stark apparatus. The solvent was evaporated and the residue was dissolved in ether, washed with water (three times) and brine (three times). The organic layer was dried with sodium sulfate, filtered, concentrated and the residue was purified by distillation to obtain in 80% yield 1-bromo-2-[bis(4-fluorophenyl)methoxy]ethane, b.p. 170° C. at 0.1 mm Hg.

1-Bromo-2-[bis(4-fluorophenyl)methoxy]ethane was refluxed overnight under nitrogen in N,N-dimethylformamide (0.5 l for 0.1 mol of compound) with an equimolar amount of phthalimide and dry potassium carbonate at 120° C. After cooling the solid material was filtered off, the filtrate was concentrated and the organic residue was dissolved in dichloromethane. This solution was washed with 0.2N sodium hydroxide solution (two times) and then with water, dried and evaporated. The solid was triturated with ether and the phthalimido derivative was collected by filtration (yield 80%).

0.017 Mol of this phthalimido derivative was dissolved in ethanol and hydrazine hydrochloride (0.088 mol) was added. The mixture was heated at 100° C. for three hrs., then the reaction mixture was cooled, the phthalhydrazide formed during the reaction was removed by filtration and the filtrate was concentrated. The amino derivative obtained was purified by transforming it in ether into the hydrochloride to yield 70% of 2-[bis(4-fluorophenyl)methoxy]ethanamine hydrochloride. Equimolar amounts of 2-[bis(4-fluorophenyl)methoxy]-ethanamine hydrochloride, benzeneethanal and NaBH3CN were dissolved in dry tetrahydrofuran (50 ml for 0.01 mol) and a few ml of methanol were also added. The mixture was left at room temperature with stirring overnight. The solid material was filtered off, the filtrate was evaporated and the residue was dissolved in dichloromethane. This solution was dried with sodium sulfate, filtered and concentrated. The compound was purified by flash column chromatography by using a mixture of petroleum ether/ethyl acetate in a ratio 7:3 increasing to 6:4. The eluent was previously saturated with ammonia gas. The free base obtained was transformed into the (Z)-2-butenedioate by adding maleic acid in ether, which was crystallized from a mixture of ether and methanol (10:1) to give N-[2-(bis(4-fluorophenyl)-methoxy)ethyl]benzeneethanamine (Z)-2-butenedioate (1:1) salt. m.p. 145°–147° C.

EXAMPLE 4

In an analogous manner as described in Example 3 was prepared:

N-[2-(bis(4-fluorophenyl)methoxy)ethyl]-2-(trifluoromethyl)-benzeneethanamine (Z)-2-butenedioate (1:1) salt.

N-[2-(bis(4-fluorophenyl)methoxy)ethyl]-3-(trifluoromethyl)benzeneethanamine (Z)-2-butenedioate (1:1) salt.

N-[2-(diphenylmethoxy)ethyl]-2-(trifluoromethyl)benzene-ethanamine (Z)-2-butenedioate (1:1) salt.

N-[2-(diphenylmethoxy)ethyl]-2-fluorobenzeneethanamine (Z)-2-butenedioate (1:1) salt.

2-chloro-N-[2-(diphenylmethoxy)ethyl]benzeneethanamine (Z)-2-butenedioate (1:1) salt.

EXAMPLE 5

The compounds of the invention can alternatively be prepared as follows:

N-[2-(bis(4-fluoroohenyl)methylthio)ethyl]-3-(trifluoromethyl)benzeneethanamine 18 g (0.088 mol) of 3-(trifluoromethyl)benzeneacetic acid were dissolved in 100 ml of toluene and refluxed in the presence of 0.1 mol thionylchloride for 2 h. The toluene was evaporated together with the excess of thionylchloride. The residue was dissolved in toluene (25 ml) and added dropwise to 19.66 g (0.088 mol) of 2-[bis(4-fluorophenyl)methylthio]ethaneamine in 25 ml of toluene. The mixture was refluxed for 3 h, after which the warm solution was poured out into a mixture of water, acetic acid, and chloroform. The organic layer was washed with acetic acid, aq. sodium hydroxide, and water, and dried over sodium sulfate. After evaporation of the solvent, the residue was crystallized from petroleum ether. The amide obtained (0.05 mol) was stirred for 12 h at room temperature with freshly prepared triethyloxonium fluoroborate (0.06 mol) in dichloromethane (100 ml). The solvent was evaporated, and replaced by abs. ethanol (100 ml), cooled in an ice bath, and sodium borohydride (0.12 mol) was added in small portions under stirring at a temperature below 10° C. After completion of the addition, the mixture was stirred for another 3 h at room temperature, after which time 0.01N hydrochloric acid was added. The solvents were removed, the residue was dissolved in dichloromethane, and the solution was made alkaline with 5% aq. sodium hydroxide. The organic layer was separated, dried over sodium sulfate, and concentrated, after which the residue was purified by silica chromatography to give N-[2-(bis(4-fluorophenyl)methylthio)ethyl]-3-(trifluoromethyl)benzeneethanamine in 40% yield.

We claim:

1. A benzhydryl derivative having the formula

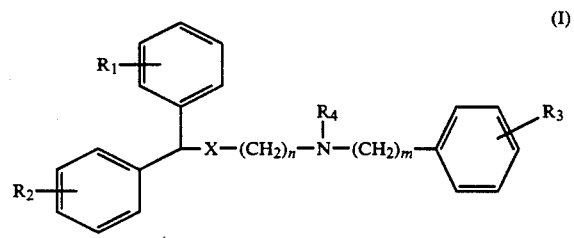

wherein
each of the groups $R_1$, $R_2$, and $R_3$ represents one to four substituents independently selected from the group consisting of hydrogen, lower alkyl, halogen, and $CF_3$, and at least one of the groups $R_1$, $R_2$, and $R_3$ is a halogen or $CF_3$;
lower alkyl is an alkyl group selected from the group consisting of methyl, ethyl, propyl, isopropyl, butyl, sec-butyl and tert-butyl;

$R_4$ represents hydrogen or methyl;

n is 2, 3, or 4;

m is 1, 2, or 3; and

X represents S;

or its pharmaceutically acceptable salts.

2. The benzhydryl derivative according to claim 1, wherein $R_3$ is $CF_3$.

3. The benzhydryl derivative according to claim 1, wherein n and m are independently 2 or 3.

4. The benzhydryl derivative according to claim 2, wherein $R_3$ is $CF_3$.

5. A pharmaceutical preparation with calmodulin inhibitor properties comprising the benzhydryl derivative of claim 1, admixed with pharmaceutically acceptable auxiliaries.

6. A method of treating a mammal for angina or ischaemia comprising administering to said mammal a therapeutically effective amount of the pharmaceutical preparation of claim 5 to inhibit calmodulin activity.

* * * * *